(12) United States Patent
Scicluna

(10) Patent No.: US 9,314,077 B2
(45) Date of Patent: Apr. 19, 2016

(54) CHECKPOINT-FRIENDLY BAG FOR A LAPTOP COMPUTER

(75) Inventor: Paul V. Scicluna, Penndel, PA (US)

(73) Assignee: Tumi, Inc., South Plainfield, NJ (US)

( * ) Notice: Subject to any disclaimer, the term of this patent is extended or adjusted under 35 U.S.C. 154(b) by 0 days.

(21) Appl. No.: 12/381,997

(22) Filed: Mar. 18, 2009

(65) Prior Publication Data

US 2010/0236885 A1    Sep. 23, 2010

(51) Int. Cl.
| | |
|---|---|
| *A45C 3/00* | (2006.01) |
| *A45C 11/00* | (2006.01) |
| *A45C 7/00* | (2006.01) |
| *A45C 13/10* | (2006.01) |

(52) U.S. Cl.
CPC .............. *A45C 11/00* (2013.01); *A45C 7/0045* (2013.01); *A45C 7/0054* (2013.01); *A45C 7/0086* (2013.01); *A45C 7/0095* (2013.01); *A45C 13/103* (2013.01); *A45C 2003/005* (2013.01); *A45C 2011/003* (2013.01); *G01N 2223/611* (2013.01)

(58) Field of Classification Search
CPC ............ A45C 13/02; A45C 5/00; A45C 3/00; A45C 3/02; A45C 5/14
USPC ............... 190/100–109; 224/220, 417, 42.11, 224/429, 575, 578; 206/287.1, 279, 320
See application file for complete search history.

(56) References Cited

U.S. PATENT DOCUMENTS

| | | | |
|---|---|---|---|
| 4,598,803 A * | 7/1986 | Ghiassi | A45C 7/0086 190/102 |
| 5,010,988 A | 4/1991 | Brown | |
| D360,978 S | 8/1995 | Willard et al. | |
| 5,505,297 A * | 4/1996 | Myers | A45C 3/004 190/125 |
| 5,676,223 A | 10/1997 | Cunningham | |
| D401,057 S * | 11/1998 | Rausch | D3/231 |
| 6,098,769 A * | 8/2000 | Yen | A45C 5/14 190/102 |
| D432,311 S | 10/2000 | Weinreb | |

(Continued)

FOREIGN PATENT DOCUMENTS

| | | |
|---|---|---|
| GB | 2434085 | 7/2007 |
| GB | 2434085 A | 7/2007 |

*Primary Examiner* — Fenn Mathew
*Assistant Examiner* — Cynthia Collado
(74) *Attorney, Agent, or Firm* — Lando & Anastasi, LLP

(57) ABSTRACT

A checkpoint-friendly bag for allowing a laptop computer stored in a dedicated portion thereof to provide a clear, unobstructed, and distinct image thereof when X-ray screened at an inspection station without having to remove the laptop computer from the dedicated portion. The bag includes a dedicated compartment and a non-dedicated compartment. The non-dedicated compartment stores items other than the laptop computer. The dedicated compartment stores only the laptop computer itself, is hingedly attached to the non-dedicated compartment at a common edge, is free of metallic snaps, zippers, and buckles, is free of pockets, and has a non-screening mode where it is replaceably fastened in side-by-side relationship to the non-dedicated compartment at discrete and spaced-apart points so as to facilitate unfastening the dedicated compartment from the non-dedicated compartment, and a screening mode where it is unfastened from the non-dedicated compartment and unfolded therefrom to lie unobstructed, flat, and coplanar with the non-dedicated compartment on the inspection station so as to allow the laptop computer stored in the dedicated compartment to provide the clear, unobstructed, and distinct image thereof when X-ray screened at the inspection station without having to remove the laptop computer from the dedicated compartment.

13 Claims, 4 Drawing Sheets

(56) References Cited

U.S. PATENT DOCUMENTS

| | | | |
|---|---|---|---|
| 6,213,267 B1 * | 4/2001 | Miller | A45C 7/0086 190/102 |
| D443,983 S | 6/2001 | Hillman | |
| 6,385,897 B1 | 5/2002 | Klabunde | |
| 7,293,635 B2 | 11/2007 | Repke | |
| 7,322,477 B2 * | 1/2008 | Schweitz | A45C 7/009 150/111 |
| 7,360,379 B1 | 4/2008 | Lopez | |
| 2003/0173384 A1 * | 9/2003 | Clark | A45C 3/00 224/314 |
| 2004/0217027 A1 | 11/2004 | Harris et al. | |
| 2006/0090976 A1 | 5/2006 | Repke et al. | |
| 2007/0164068 A1 * | 7/2007 | Godshaw | B62J 9/008 224/430 |
| 2008/0050051 A1 * | 2/2008 | Palt | F17C 13/084 383/41 |
| 2009/0314594 A1 * | 12/2009 | Harrison | A45C 3/02 190/109 |

* cited by examiner

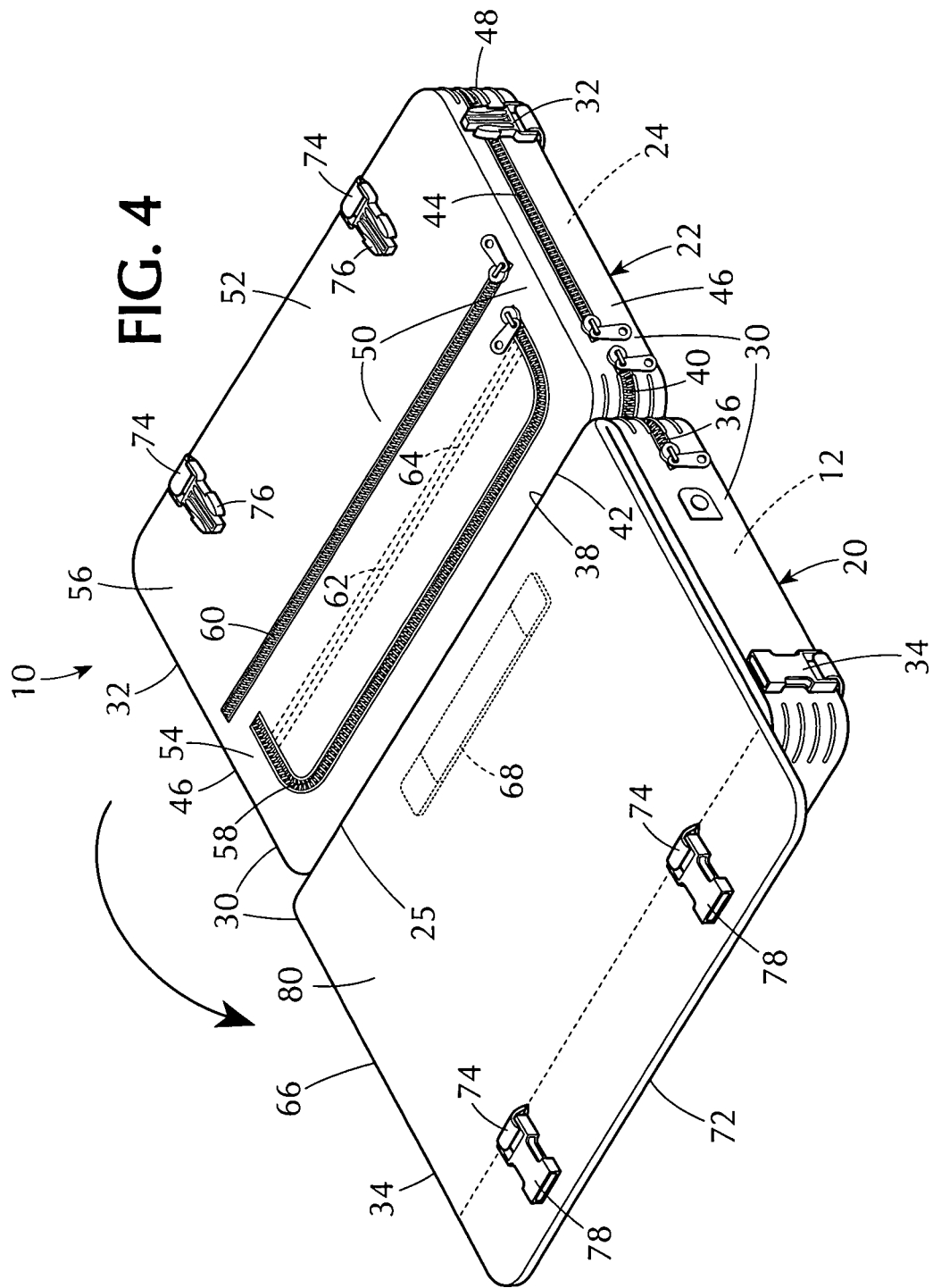

CHECKPOINT-FRIENDLY BAG FOR A LAPTOP COMPUTER

1. THE BACKGROUND OF THE INVENTION

A. The Field of the Invention

The embodiments of the present invention relate to a bag for a laptop computer, and more particularly, the embodiments of the present invention relate to a checkpoint-friendly bag for allowing a laptop computer stored in a dedicated portion thereof to provide a clear, unobstructed, and distinct image thereof when X-ray screened at an inspection station without having to remove the laptop computer from the dedicated portion.

B. The Description of the Prior Art

Since 9/11, the world of public transportation has changed significantly. In fact, there is now a government agency—the Transportation Security Agency ("TSA")—that is responsible for the heightened security at airports and other facilities. The security measures taken by TSA personnel to check each passenger and all packages carried on-board airplanes has resulted in long lines and increased pre-flight boarding times.

While TSA personnel use sophisticated instruments to determine the absence of illegal compounds and objects, there remains a requirement for visual inspection of certain devices. Packages, boxes, and carry-on bags must be opened for these visual inspections. Because the airlines have been permitting passengers to carry on just about anything, opening and closing of these articles adds to the delays of clearing security points.

The laptop computer has become a normal accessory for many travelers, both for work and entertainment during a trip. The conventional laptop computer has no integrated carrying devices, and therefore, usually is placed in a carry case. Most cases have various pockets and compartments to carry peripheral equipment and other things the owner may include with the laptop computer. The carrying cases may be made of soft or hard materials, which may be padded and completely enclose the laptop computer for protection.

To help streamline the security process and better protect laptops, the TSA now allows passengers to leave their laptop computers in bags that meet the "checkpoint friendly" standards. For a bag to be considered "checkpoint friendly," it should meet the following standards:

Have a designated laptop-only section;
Allow the laptop-only section to completely unfold to lie flat on the X-ray belt;
Have no metal snaps, zippers, or buckles inside, underneath, or on top of the laptop-only section;
Have no pockets on the inside or outside of the laptop-only section; and
Have nothing packed in the laptop-only section other than the laptop computer itself.

Thus, there exists a need for a laptop bag to be checkpoint friendly by having a designated laptop-only section, by allowing the laptop-only section to completely unfold to lie flat on the X-ray belt, by having no metal snaps, zippers, or buckles inside, underneath, or on top of the laptop-only section, by having no pockets on the inside or outside of the laptop-only section, and by having nothing packed in the laptop-only section other than the laptop computer itself.

Numerous innovations for laptop computer bags have been provided in the prior art, which will be described below in chronological order to show advancement in the art, and which are incorporated herein by reference thereto. Even though these innovations may be suitable for the individual purposes which they address, nevertheless, they differ from the embodiments of the present invention in that they do not teach a checkpoint-friendly bag for allowing a laptop computer stored in a dedicated portion thereof to provide a clear, unobstructed, and distinct image thereof when X-ray screened at an inspection station without having to remove the laptop computer from the dedicated portion.

(1) The U.S. Pat. No. 5,010,988 to Brown.

The U.S. Pat. No. 5,010,988 issued to Brown on Apr. 30, 1991 in U.S. class 190 and subclass 104 teaches a carrying case specifically adapted for use in carrying laptop computers, printers, fax machines, and the like, and which includes a case having an outer shell formed of a durable waterproofed material and a case interior including a main storage compartment and a secondary storage compartment. An expansion zone formed on a surrounding side wall structure allows the secondary storage compartment to be adjustable between a collapsed stowed position and an expanded operative position, thereby providing a second compartment to store computer equipment. The carrying case further includes a shock barrier construction defined by a layer of shock absorbent material fitted between the exterior shell and an inner lining in surrounding protecting relation to the case interior.

(2) The U.S. Pat. No. Des. 360,978 to Willard et al.

The U.S. Pat. No. Des. 360,978 issued to Willard et al. on Aug. 8, 1995 in U.S. Class D3 and subclass 301 teaches the ornamental design for a laptop computer case.

(3) The U.S. Pat. No. 5,676,223 to Cunningham.

The U.S. Pat. No. 5,676,223 issued to Cunningham on Oct. 14, 1997 in U.S. Class 190 and subclass 109 teaches a business case including a front compartment, a middle compartment, an expandable rear compartment, a removable portable computer carrying case designed to carry a portable computer, and a suit carrier. The bag member can be dropped into one of two panels located on the front face of the front compartment. The panels additionally allow for easy access to a portable computer and related accessories stored within the carrying case. Alternatively, the carrying case can be closed and stored in the expandable rear compartment when the suit carrier is stored in the front compartment of the case. The middle compartment is sized to hold clothing and travel related items for business trips and is equipped with pouches for smaller items. Furthermore, the middle compartment of the housing may include wheels, handles, and feet for easily moving and balancing the case.

(4) The U.S. Pat. No. Des. 432,311 to Weinreb.

The U.S. Pat. No. Des. 432,311 issued to Weinreb on Oct. 24, 2000 in U.S. class D3 and subclass 319 teaches the ornamental design for a lap top computer carrying case.

(5) The U.S. Pat. No. 6,213,267 B1 to Miller.

The U.S. Pat. No. 6,213,267 B1 issued to Miller on Apr. 10, 2001 in U.S. class 190 and subclass 108 teaches a portable luggage carrying case having a detachable carry tote portion capable of housing a laptop computer and various computer accessories. The detachable carry tote is joined to the main portion of the luggage enclosure via a zipper situated around the periphery of the main portion and the carry tote. Once separated from the main portion, the carry tote, including an upper and a lower section joined together along its adjacent edges via material along the inner-facing surface of each section, can be folded, and a securing zipper used to secure the upper and lower portions to each other in a face-to-face configuration. The carry tote, with a laptop computer stored within one of its zippered pouches can now be utilized separately and independently from the main portion of the luggage enclosure. A zipper secures the carry tote bag sections to each other, and also is used to join the main portion with the detachable portion of the luggage enclosure, thereby eliminating the need for an additional zipper or joining apparatus. A combination luggage carrying case and portable computer storage case are in one unit.

(6) The U.S. Pat. No. Des. 443,983 S to Hillman.

The U.S. Pat. No. Des. 443,983 S issued to Hillman on Jun. 26, 2001 in U.S. class D3 and subclass 276 teaches the ornamental design for a notebook computer case.

(7) The United States Patent Application Publication Number US 2004/0217027A1 to Harris et al.

The United States Patent Application Publication Number US 2004/0217027 A1 published to Harris et al. on Nov. 4, 2004 in U.S. class 206 and subclass 320 teaches a carrying case for a computer, which is made of webbing to permit security personnel to view the computer without removing it from the case. The laptop can be opened and used without removing the case.

(8) The United States Patent Application Publication Number US 2006/0090976 A1 to Repke et al.

The United States Patent Application Publication Number US 2006/0090976 A1 published to Repke et al on May 4, 2006 in U.S. class 190 and subclass 110 teaches a travel bag for organizing a computer and other items, which has a computer compartment that includes pockets for small items and a dual-entry pocket. Flat pockets are provided on two large sides of the dual-entry pocket. An opening on the outer body of the bag provides access to contents of the dual-entry pocket and flat pockets. The flat pockets are made of elastic material for securely holding small items and devices that are frequently retrieved, such as a cell phone, travel tickets, sunglasses, etc. A briefcase style includes a retractable flap that covers the top of the bag and slides down into the bag to provide unfettered access to contents. A tote style has deep pockets in expandable side gussets for holding a water bottle, an umbrella, shoes, etc. Straps are rope-filled tubular leather. A cord kit, a tool kit, and a purse may be included.

(9) The United Kingdom Patent Application Publication Number GB 2434085 A to Roberts.

The United Kingdom Patent Application Publication Number GB 2434085 A published to Roberts on Jul. 18, 2007 in UK class A4G teaches a carrying bag for a computer, which includes a support structure attached to the top surface of the bag. The support structure is arranged so as to keep the computer spaced from the bottom wall of the bag. The support structure is, preferably, attached to the top wall by rivets. The support structure may include first and second segments that may be elasticised and that can be adjustably secured together by a buckle. In use, the support structure holds the computer in isolation from the bottom wall of the carrying bag and acts to absorb any energy transferred to the bag in the event that the bag collides with an external surface.

(10) The U.S. Pat. No. 7,293,635 B2 to Repke et al.

The U.S. Pat. No. 7,293,635 B2 issued to Repke et al. on Nov. 13, 2007 in U.S. class 190 and subclass 109 teaches a travel bag for organizing a computer and other items, which has a computer compartment that includes pockets for small items and a dual-entry pocket. Flat pockets are provided on two large sides of the dual-entry pocket. An opening on the outer body of the bag provides access to contents of the dual-entry pocket and flat pockets. The flat pockets are made of elastic material for securely holding small items and devices that are frequently retrieved, such as a cell phone, travel tickets, sunglasses, etc. A briefcase style includes a retractable flap that covers the top of the bag and slides down into the bag to provide unfettered access to contents. A tote style has deep pockets in expandable side gussets for holding a water bottle, umbrella, shoes, etc. Straps are rope-filled tubular leather. A cord kit, a tool kit, and a purse may be included.

(11) The U.S. Pat. No. 7,360,379 B1 to Lopez.

The U.S. Pat. No. 7,360,379 B1 issued to Lopez on Apr. 22, 2008 in U.S. class 70 and subclass 58 teaches a laptop computer securing system that includes a luggage case having a bottom wall and a peripheral wall that is attached to and extends upwardly from the bottom wall. The peripheral wall has an upper edge defining an opening into the luggage case. A cover is pivotally coupled to the upper edge and is selectively positionable in a closed position extending over and closing the opening. A closure is attached to the cover to selectively secure the cover in the closed position. A cable has a first end and a second end. The cable is attached to the peripheral wall. The cable extends into the luggage case from the peripheral wall. A locking assembly is attached to the second end of the cable, and is configured to be extended into and releasably locked to a laptop computer.

It is apparent that numerous innovations for laptop bags have been provided in the prior art that are adapted to be used. Furthermore, even though these innovations may be suitable for the individual purposes which they address, nevertheless, they would not be suitable for the purposes of the embodiments of the present invention as heretofore described, namely, a checkpoint-friendly bag for allowing a laptop computer stored in a dedicated portion thereof to provide a clear, unobstructed, and distinct image thereof when X-ray screened at an inspection station without having to remove the laptop computer from the dedicated portion.

2. SUMMARY OF THE INVENTION

Thus, an object of the embodiments of the present invention is to provide a checkpoint-friendly bag for allowing a laptop computer stored in a dedicated portion thereof to provide a clear, unobstructed, and distinct image thereof when X-ray screened at an inspection station without having to remove the laptop computer from the dedicated portion, which avoids the disadvantages of the prior art.

Briefly stated, another object of the embodiments of the present invention is to provide a checkpoint-friendly bag for allowing a laptop computer stored in a dedicated portion thereof to provide a clear, unobstructed, and distinct image thereof when X-ray screened at an inspection station without having to remove the laptop computer from the dedicated portion. The bag includes a dedicated compartment and a non-dedicated compartment. The non-dedicated compartment stores items other than the laptop computer. The dedicated compartment stores only the laptop computer itself, is hingedly attached to the non-dedicated compartment at a common edge, is free of metallic snaps, zippers, and buckles, is free of pockets, and has a non-screening mode where it is replaceably fastened in side-by-side relationship to the non-dedicated compartment at discrete and spaced-apart points so as to facilitate unfastening the dedicated compartment from the non-dedicated compartment, and a screening mode where it is unfastened from the non-dedicated compartment and unfolded therefrom to lie unobstructed, flat, and coplanar with the non-dedicated compartment on the inspection station so as to allow the laptop computer stored in the dedicated compartment to provide the clear, unobstructed, and distinct image thereof when X-ray screened at the inspection station without having to remove the laptop computer from the dedicated compartment.

The novel features considered characteristic of the embodiments of the present invention are set forth in the appended claims. The embodiments of the present invention themselves, however, both as to their construction and their method of operation together with additional objects and advantages thereof will be best understood from the following description of the specific embodiments when read and understood in connection with the accompanying drawing.

3. BRIEF DESCRIPTION OF THE DRAWING

The figures of the drawing are briefly described as follows:

FIG. 4 is a diagrammatic perspective view of the checkpoint-friendly bag with the flap pivoted to be over the dedicated compartment.

4. LIST OF REFERENCE NUMERALS UTILIZED IN THE DRAWING

Figure 1:
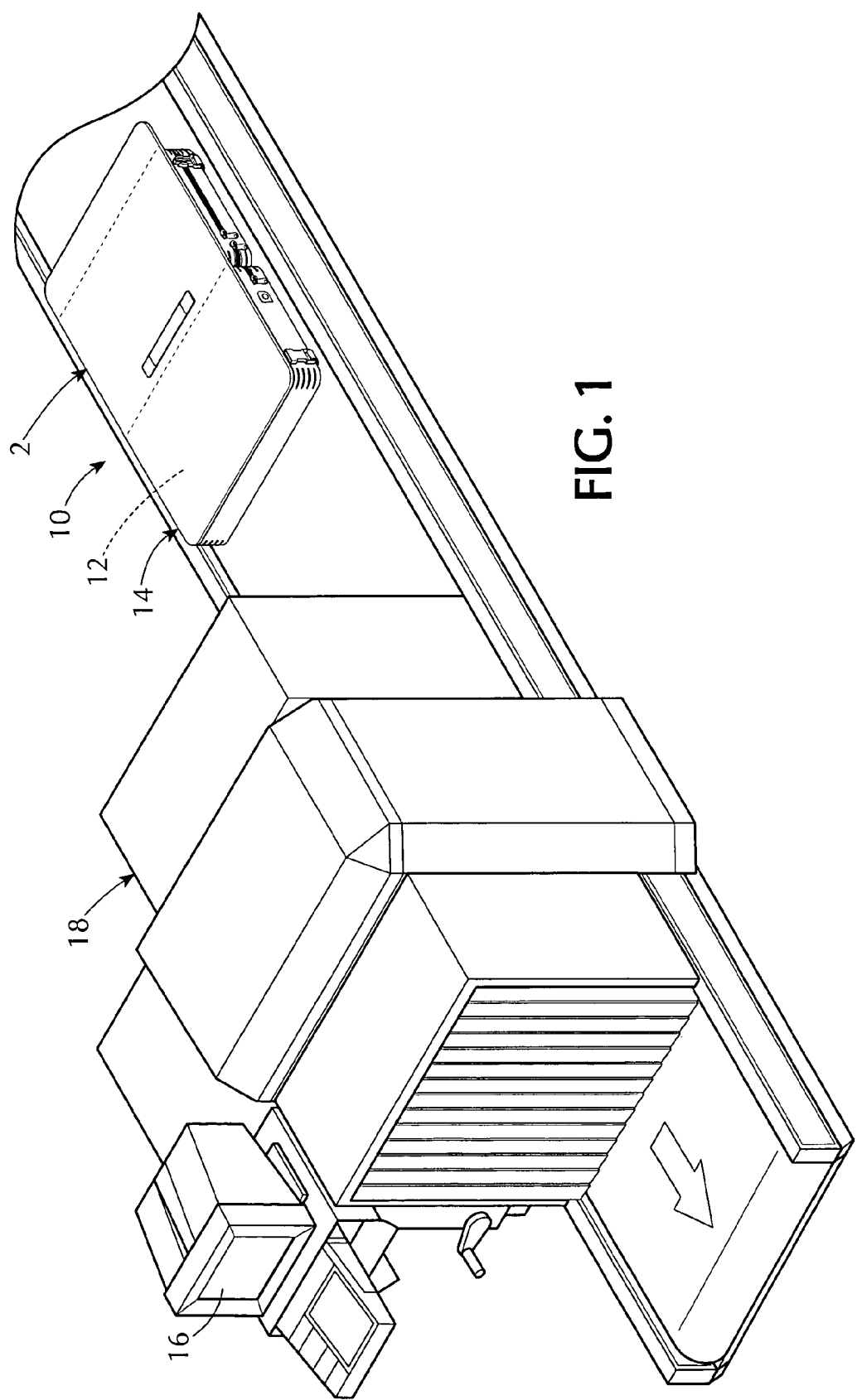
FIG. 1 is a diagrammatic perspective view of the checkpoint-friendly bag of the embodiments of the present invention allowing a laptop computer stored in a dedicated portion thereof to provide a clear, unobstructed, and distinct image thereof when X-ray screened at an inspection station without having to remove the laptop computer from the dedicated portion.

A. General.
10 checkpoint-friendly bag of embodiments of present invention for allowing laptop computer 12 stored in dedicated portion 14 thereof to provide clear, unobstructed, and distinct image 16 thereof when X-ray screened at inspection station 18 without having to remove laptop computer 12 from dedicated portion 14
12 laptop computer
14 dedicated portion
16 clear, unobstructed, and distinct image
18 inspection station
B. Configuration of Checkpoint-Friendly Bag 10.
20 dedicated compartment for storing only laptop computer 12 itself
22 non-dedicated compartment for storing items 24 other than laptop computer 12
24 items other than laptop computer 12
25 common edge of dedicated compartment 20 and non-dedicated compartment 22
26 discrete and spaced-apart points
28 first pair of quick release buckles of discrete and spaced-apart points 26
30 adjacent side walls of dedicated compartment 20 and non-dedicated compartment 22
32 male portion of each first quick release buckle of first pair of quick release buckles 28 of discrete and spaced-apart points 26
34 female portion of each first quick release buckle of first pair of quick release buckles 28 of discrete and spaced-apart points 26
36 first non-metallic zipper of dedicated compartment 20 for accessing laptop computer 12
38 top wall of dedicated compartment 20
40 second non-metallic zipper of non-dedicated compartment 22 for accessing items 24 other than laptop computer 12
42 top wall of non-dedicated compartment 22
44 third non-metallic zipper of non-dedicated compartment 22
46 side walls of non-dedicated compartment 22
48 bottom wall of non-dedicated compartment 22
50 pair of flat, expandable, side gusset pockets of non-dedicated compartment 22 for storing items 24 other than laptop computer 12
52 outer wall of non-dedicated compartment 22
54 upper portion of outer wall 52 of non-dedicated compartment 22
56 lower portion of outer wall 52 of non-dedicated compartment 22
58 fourth non-metallic zipper of non-dedicated compartment 22
60 fifth non-metallic zipper of non-dedicated compartment 22
62 third flat, expandable, side gusset pocket in non-dedicated compartment 22 for storing items 24 other than laptop computer 12
64 sixth non-metallic zipper for accessing third flat, expandable, side gusset pocket 62 in non-dedicated compartment 22
66 flap
68 handle
70 outer wall of flap 66
72 free end of flap 66
74 second pair of quick release buckles
76 male portion of each second quick release buckle of second pair of quick release buckles 74
78 female portion of each second quick release buckle of second pair of quick release buckles 74
80 inner wall of flap 66
82 shoulder strap

5. DETAILED DESCRIPTION OF THE PREFERRED EMBODIMENTS

A. General.

Referring now to the figures, in which like numerals indicate like parts, and particularly to FIG. 1, which is a diagrammatic perspective view of the checkpoint-friendly bag of the embodiments of the present invention allowing a laptop computer stored in a dedicated portion thereof to provide a clear, unobstructed, and distinct image thereof when X-ray screened at an inspection station without having to remove the laptop computer from the dedicated portion, the checkpoint-friendly bag of the embodiments of the present invention is shown generally at 10 for allowing a laptop computer 12 stored in a dedicated portion 14 thereof to provide a clear, unobstructed, and distinct image 16 thereof when X-ray screened at an inspection station 18 without having to remove the laptop computer 12 from the dedicated portion 14.

B. The Configuration of the Checkpoint-Friendly Bag 10.

Figure 2:
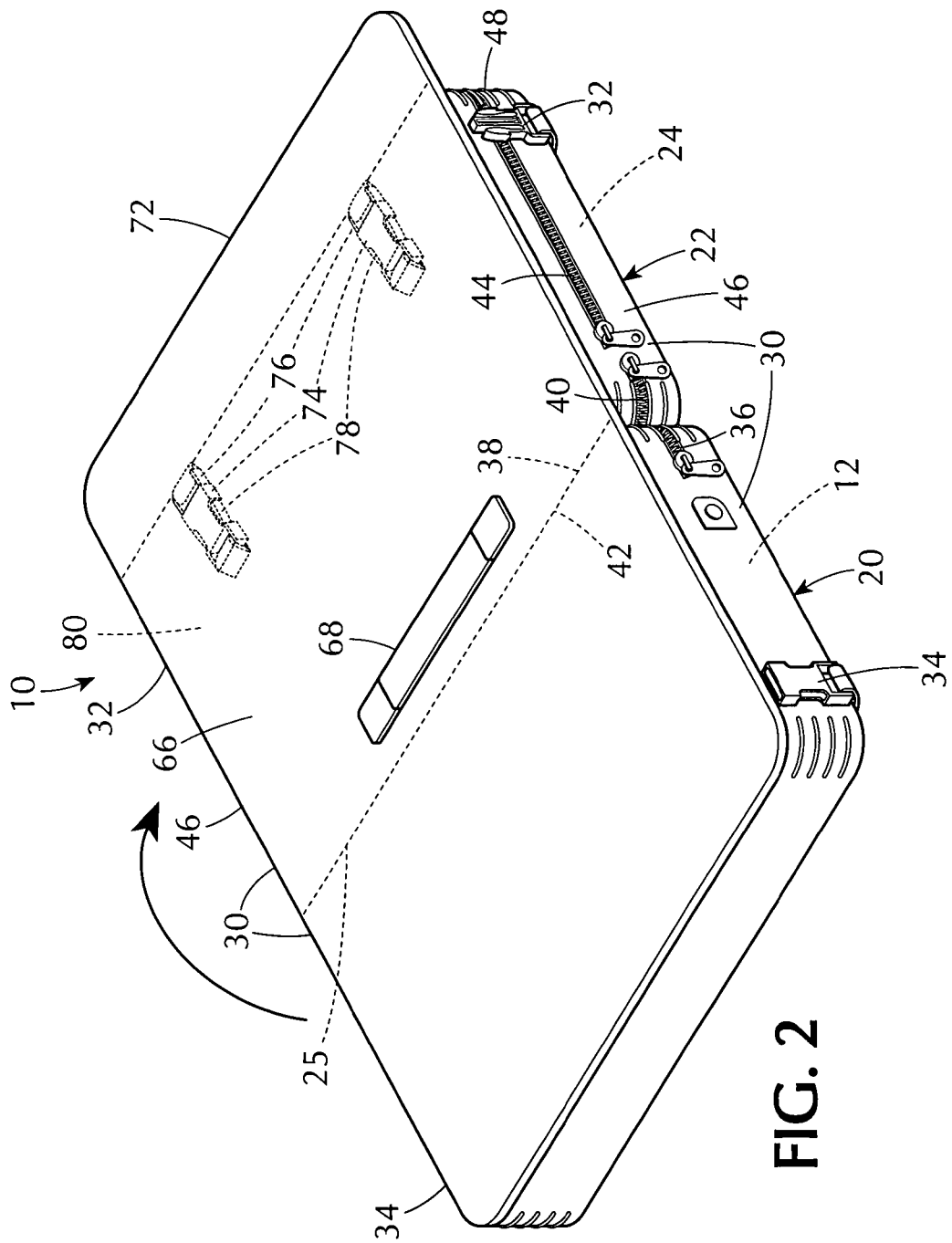
FIG. 2 is an enlarged diagrammatic perspective view of the checkpoint-friendly bag in the X-ray screening mode identified by ARROW 2 in FIG. 1 with the flap pivoted to be over the non-dedicated compartment.
Figure 3:
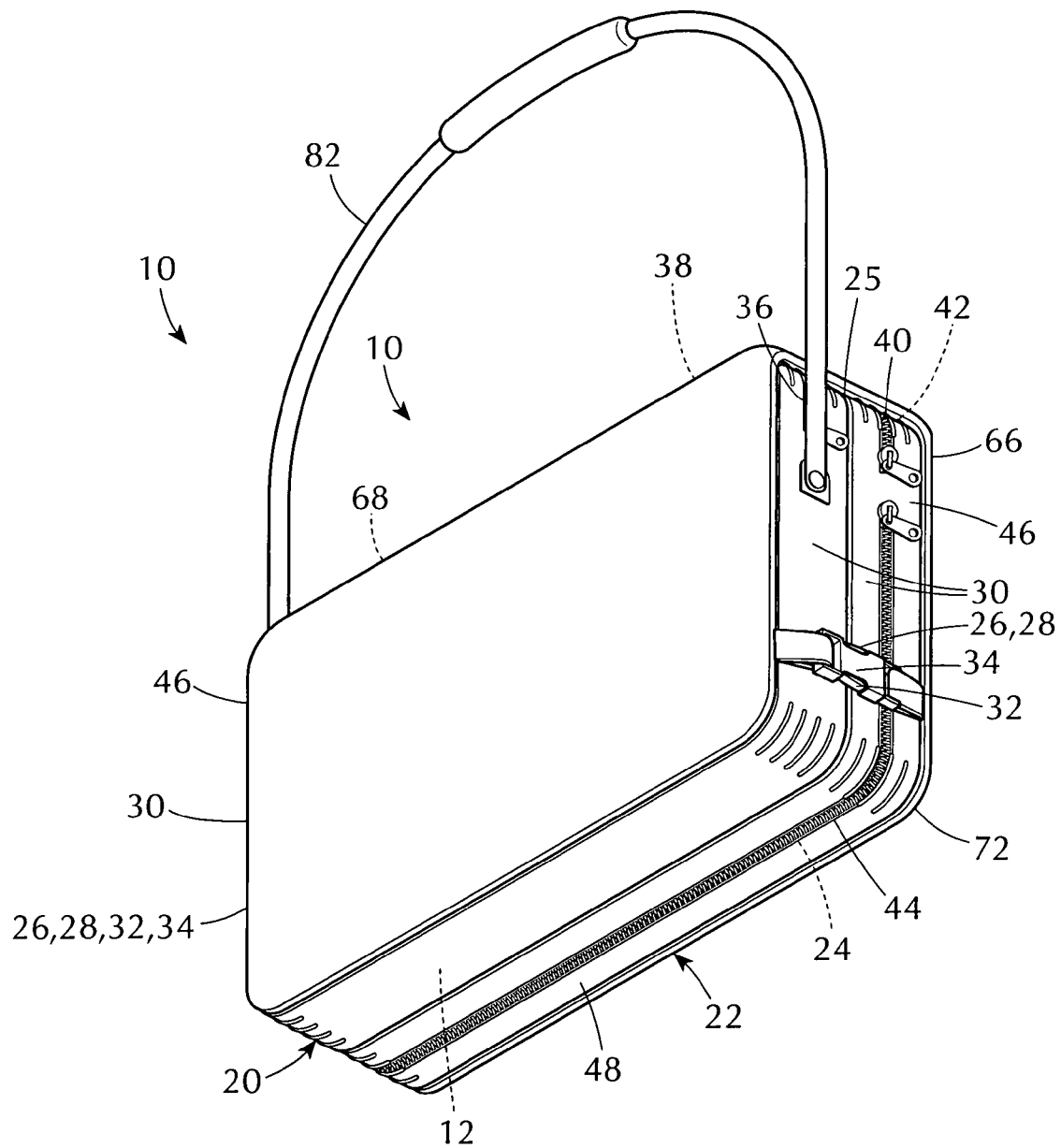
FIG. 3 is a diagrammatic perspective view of the checkpoint-friendly bag in the non-X-ray screening mode.

The configuration of the checkpoint-friendly bag 10 can best be seen in FIGS. 2-4, which are, respectively, an enlarged diagrammatic perspective view of the checkpoint-friendly bag in the X-ray screening mode identified by ARROW 2 in FIG. 1 with the flap pivoted to be over the non-dedicated compartment, a diagrammatic perspective view of the checkpoint-friendly bag in the non-X-ray screening mode, and a diagrammatic perspective view of the checkpoint-friendly bag with the flap pivoted to be over the dedicated compartment, and as such, will be discussed with reference thereto.

As shown in FIGS. 2-4, the checkpoint-friendly bag 10 comprises a dedicated compartment 20 and a non-dedicated compartment 22. The non-dedicated compartment stores items other than the laptop computer. The dedicated compartment 20 stores only the laptop computer 12 itself, is hingedly attached to the non-dedicated compartment 22 at a common edge 25, is free of metallic snaps, zippers, and buckles, is free of pockets, and has a non-screening mode where it is replaceably fastened in side-by-side relationship to the non-dedicated compartment 22 at discrete and spaced-apart points 26 so as to facilitate unfastening the dedicated compartment 20 from the non-dedicated compartment 22, and a screening mode where it is unfastened from the non-dedicated compartment 22 and unfolded therefrom to lie unobstructed, flat, and coplanar with the non-dedicated compartment 22 on the inspection station 18 so as to allow the laptop computer 12 stored in the dedicated compartment 20 to provide the clear, unobstructed, and distinct image 16 thereof when X-ray screened at the inspection station 18 without having to remove the laptop computer 12 from the dedicated compartment 20.

As further shown in FIGS. 2-4, the discrete and spaced-apart points 26 comprises a first pair of quick release buckles 28. Each first quick release buckle 28 is disposed on adjacent side walls 30 of the dedicated compartment 20 and the non-dedicated compartment 22, respectively, so as to facilitate unfastening the dedicated compartment 20 from the non-dedicated compartment 22 when obtaining the screening mode is desired.

As further shown in FIGS. 2-4, each first quick release buckle 28 of the discrete and spaced-apart points 26 comprises a male portion 32 and a female portion 34 that are disposed on the adjacent side walls 30 of the dedicated compartment 20 and the non-dedicated compartment 22, respectively.

As further shown in FIGS. 2-4, the dedicated compartment 20 is accessible for the laptop computer 12 via a first non-metallic zipper 36. The first non-metallic zipper 36 is disposed on a top wall 38 of the dedicated compartment 20, adjacent to the common edge 25.

As further shown in FIGS. 2-4, the non-dedicated compartment 22 is accessible for the items 24 other than the laptop computer 12 via a second non-metallic zipper 40. The second non-metallic zipper 40 is disposed on a top wall 42 of the non-dedicated compartment 22, adjacent to the common edge 25.

As further shown in FIGS. 2-4, the non-dedicated compartment 22 is expandable via a third non-metallic zipper 44. The third non-metallic zipper 44 is disposed continuously on side walls 46 and a bottom wall 48 of the non-dedicated compartment 22.

As shown in FIG. 4, the non-dedicated compartment 22 further comprises a pair of flat, expandable, side gusset pockets 50. The pair of flat, expandable, side gusset pockets 50 are disposed on an outer wall 52 of the non-dedicated compartment 22, at an upper portion 54 thereof and at a lower portion 56 thereof, respectively, for storing the items 24 other than the laptop computer 12.

As further shown in FIG. 4, the pair of flat, expandable, side gusset pockets 50 of the non-dedicated compartment 22 are accessible via a fourth non-metallic zipper 58 and a fifth non-metallic zipper 60, respectively, (FIG. 4).

As further shown in FIG. 4, the flat, expandable, side gusset pocket 50 on the upper portion 54 of the outer wall 52 of the non-dedicated compartment 22 harbors a third flat, expandable, side gusset pocket 62 therein. The third flat, expandable, side gusset pocket 62 is accessible for the items 24 other than the laptop computer 12 via a sixth non-metallic zipper 64.

As further shown in FIGS. 2-4, the checkpoint-friendly bag 10 further comprises a flap 66. The flap 66 is hingedly attached to the dedicated compartment 20, adjacent to the common edge 25, and overlies the outer wall 52 of the non-dedicated compartment 22 when in the X-ray screening mode, but overlies the dedicated compartment 20 when in the non-screening mode and access to any of the pair of flat, expandable, side gusset pockets 50 and the third flat, expandable, side gusset pocket 62 is required.

As further shown in FIGS. 2 and 4, the checkpoint-friendly bag 10 further comprises a handle 68. The handle 68 is attached to the flap 66, on an outer wall 70 thereof, and is offset from center towards its free end 72.

As further shown in FIGS. 2 and 4, the checkpoint-friendly bag 10 further comprises a second pair of quick release buckles 74. Each second quick release buckle 74 is disposed on the outer wall 52 of the non-dedicated compartment 22, at the lower portion 56 thereof, and on an inner wall 76 of the flap 66, adjacent to the free end 72 thereof, so as to facilitate unfastening the flap 66 from the non-dedicated compartment 22 when access to any of the pair of flat, expandable, side gusset pockets 50 and the third flat, expandable, side gusset pocket 62 is required.

As further shown in FIGS. 2 and 4, each second quick release buckle 74 comprises a male portion 76 and a female portion 78 that are disposed on the outer wall 52 of the non-dedicated compartment 22, at the lower portion 56 thereof, and on the inner wall 80 of the flap 66, respectively, adjacent to the free end 72 thereof.

As shown in FIG. 3, the checkpoint-friendly bag 10 further comprises a shoulder strap 82. The shoulder strap 82 extends replaceably from one side wall 30 of the dedicated compartment 20 to the other side wall 30 of the dedicated compartment 20.

C. The Impressions.

It will be understood that each of the elements described above or two or more together may also find a useful application in other types of constructions differing from the types described above.

While the embodiments of the present invention have been illustrated and described as embodied in a checkpoint-friendly bag for allowing a laptop computer stored in a dedicated portion thereof to provide a clear, unobstructed, and distinct image thereof when X-ray screened at an inspection station without having to remove the laptop computer from the bag, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A checkpoint-friendly bag for allowing a laptop computer to be stored therein when X-ray screened at an inspection station, without having to remove the laptop computer therefrom the bag comprising:
   a dedicated compartment for storing the laptop computer, the dedicated compartment consisting of a single closeable pocket sized and arranged for storing only a laptop computer and a single non-metallic zipper for accessing the single closeable pocket, the dedicated compartment devoid of any additional pockets, zippers, or pouches anywhere thereon, the dedicated compartment defined by four sidewalls, a first planar wall and a second planar wall, the single non-metallic zipper positioned along at least one of the sidewalls;

a non-dedicated compartment, the non-dedicated compartment comprising, a first planar wall, a second planar wall, a plurality of pockets and/or pouches in the first planar wall for storing removable articles, the non-dedicated compartment being further defined by four sidewalls, and a second non-metallic zipper positioned along at least one sidewall of the sidewalls of the non-dedicated compartment for accessing the non-dedicated compartment;

a common edge between the at least one sidewall of the dedicated compartment and the at least one sidewall of the non-dedicated compartment forming a single living hinge so that the single non-metallic zipper of the dedicated compartment faces the second non-metallic zipper of the non-dedicated compartment in a screening mode of the bag wherein the second planar wall of the dedicated compartment and the second planar wall of the non-dedicated compartment are substantially in a same plane;

an exterior portion of the at least one sidewall of the dedicated compartment with the single non-metallic zipper and an exterior portion of the at least one sidewall of the non-dedicated compartment with the second non-metallic zipper, adjacent the common edge, forming a substantially parallel planar surface when the bag is in a non-screening mode wherein the bag is folded so that the second planar wall of the dedicated compartment is adjacent the second planar wall of the non-dedicated compartment;

and a flap hingedly attached adjacent the common edge, the flap configured to overly the first planar wall of the non-dedicated compartment when the bag is in the screening mode wherein the second planar wall of the dedicated compartment and the second planar wall of the non-dedicated compartment are substantially in the same plane, the flap configured to overly the first planar surface of dedicated compartment when the bag is folded so that the second planar surface of the dedicated compartment is adjacent the second planar surface of the non-dedicated compartment so as to be in the non-screening mode.

2. The bag of claim 1, further comprising:

a first pair of quick release buckles for closing the bag when the bag is in the non-screening mode;

wherein a portion of each first quick release buckle is disposed on adjacent side walls of the dedicated compartment and the non-dedicated compartment when the bag is in the non-screening mode, respectively, so as to facilitate unfastening the dedicated compartment from the non-dedicated compartment when obtaining the screening mode is desired.

3. The bag of claim 2, further comprising a handle disposed on a first planar side of the flap and near the common edge.

4. The bag of claim 3, further comprising a second pair of quick release buckles having a portion of the quick release buckles disposed on a second planar side of the flap for facilitating fastening of the flap and the dedicated compartment to the non-dedicated compartment to provide the non-screening mode and for facilitating unfastening the flap from the non-dedicated compartment to provide the screening mode.

5. The bag of claim 4, wherein each second quick release buckle comprises a male portion and a female portion that are disposed on the first planar wall of the non-dedicated compartment and on the second planar side of the flap, respectively.

6. The bag of claim 4, further comprising a shoulder strap.

7. The bag of claim 6, wherein the shoulder strap is attached to the dedicated compartment at an attachment point of two of the sidewalls of the dedicated compartment.

8. The bag of claim 2, wherein each first quick release buckle comprises a male portion and a female portion that are disposed on the adjacent side walls of the dedicated compartment and the non-dedicated compartment.

9. The bag of claim 1, wherein the single non-metallic zipper is disposed in a top side wall of the dedicated compartment when the bag is in the non-screening mode, and the single closeable pocket is accessible for the laptop computer via the single non-metallic zipper.

10. The bag of claim 1, wherein the non-dedicated compartment comprises a closeable pocket that is accessible for articles other than the laptop computer via the second non-metallic zipper, which is disposed in a top side wall of non-dedicated compartment when the bag is in the non-screening mode.

11. The bag of claim 10, wherein the non-dedicated compartment further comprises a third non-metallic zipper disposed in at least a portion of three of the side walls other than the sidewall comprising the second non-metallic zipper of the non-dedicated compartment, so that the closeable pocket of the non-dedicated compartment is expandable via the third non-metallic zipper.

12. The bag of claim 1, wherein the non-dedicated compartment comprises a pair of flat, expandable, side gusset pockets disposed on the first planar wall of the non-dedicated compartment.

13. The bag of claim 12, wherein the non-dedicated compartment further comprises a fourth non-metallic zipper and a fifth non-metallic zipper disposed in the first planar wall of the non-dedicated compartment, so that the pair of flat, expandable, side gusset pockets of the non-dedicated compartment are accessible via the fourth non-metallic zipper and the fifth non-metallic zipper, respectively.

* * * * *